(12) United States Patent
Abe

(10) Patent No.: US 9,138,200 B2
(45) Date of Patent: Sep. 22, 2015

(54) ULTRASONIC DIAGNOSIS METHOD AND APPARATUS IMAGE PROCESSING FOR CALCULATING ROTATIONAL ANGLES IN A SPACE BY THREE-DIMENSIONAL POSITION TRACKING

(75) Inventor: Yasuhiko Abe, Otawara (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 950 days.

(21) Appl. No.: 12/548,816

(22) Filed: Aug. 27, 2009

(65) Prior Publication Data

US 2010/0056919 A1 Mar. 4, 2010

(30) Foreign Application Priority Data

Aug. 29, 2008 (JP) ................. 2008-222648

(51) Int. Cl.
*A61B 8/00* (2006.01)
*A61B 8/08* (2006.01)
*A61B 8/14* (2006.01)
*G01S 15/89* (2006.01)
*A61B 6/00* (2006.01)

(52) U.S. Cl.
CPC .............. *A61B 8/08* (2013.01); *A61B 8/0883* (2013.01); *A61B 6/503* (2013.01); *A61B 8/14* (2013.01); *A61B 8/483* (2013.01); *A61B 8/523* (2013.01); *G01S 15/8993* (2013.01)

(58) Field of Classification Search
CPC .................................................. A61B 8/0883
USPC .......... 382/131, 133; 600/437, 438, 440, 443, 600/447, 450, 454
See application file for complete search history.

(56) References Cited

U.S. PATENT DOCUMENTS 6,254,539 B1 * 7/2001 Pang et al. .................... 600/443
6,290,648 B1 * 9/2001 Kamiyama .................. 600/443
6,352,507 B1 * 3/2002 Torp et al. .................... 600/438
6,364,835 B1 * 4/2002 Hossack et al. .............. 600/443
6,554,770 B1 * 4/2003 Sumanaweera et al. ...... 600/443
6,641,536 B2 * 11/2003 Hossack et al. .............. 600/443
7,044,913 B2 * 5/2006 Shiki ............................ 600/454

(Continued)

FOREIGN PATENT DOCUMENTS

JP 11-155862 A 6/1999
JP 2003-250804 9/2003

(Continued)

OTHER PUBLICATIONS

English Translation of JP2007044499 Pub. Date Feb. 22, 2007.*

(Continued)

*Primary Examiner* — James Kish
*Assistant Examiner* — Serkan Akar
(74) *Attorney, Agent, or Firm* — Oblon, McClelland, Maier & Neustadt, L.L.P.

(57) ABSTRACT

A normal vector on a regression plane in a reference time phase in a three-dimensional space is defined with regard to a moving tissue typified by a myocardial wall. Orthogonal projection vectors on the regression plane at each vertex (Pij(t)) in each time phase are calculated by using the normal vector on the regression plane, and the angle defined by the orthogonal projection vectors is calculated, thereby acquiring a local rotational angle at each vertex (Pij(t)) in each time phase relative to the reference time phase.

24 Claims, 12 Drawing Sheets

(56) References Cited

U.S. PATENT DOCUMENTS

| | | | |
|---|---|---|---|
| 7,261,694 B2* | 8/2007 | Torp et al. | 600/443 |
| 7,722,540 B2* | 5/2010 | Abe et al. | 600/443 |
| 7,798,965 B2* | 9/2010 | Torp et al. | 600/443 |
| 7,837,625 B2* | 11/2010 | Abe | 600/454 |
| 7,841,982 B2* | 11/2010 | Johnson et al. | 600/437 |
| 2002/0177775 A1* | 11/2002 | Torp et al. | 600/443 |
| 2003/0083578 A1* | 5/2003 | Abe et al. | 600/447 |
| 2003/0097067 A1* | 5/2003 | Poland et al. | 600/443 |
| 2004/0027347 A1* | 2/2004 | Farsaie | 345/419 |
| 2005/0085729 A1* | 4/2005 | Abe | 600/450 |
| 2006/0173328 A1* | 8/2006 | Fan et al. | 600/441 |
| 2007/0038087 A1* | 2/2007 | Abe et al. | 600/437 |
| 2007/0047790 A1* | 3/2007 | Dewaele | 382/128 |
| 2008/0002873 A1* | 1/2008 | Reeves et al. | 382/133 |
| 2008/0009734 A1* | 1/2008 | Houle et al. | 600/443 |
| 2008/0069436 A1* | 3/2008 | Orderud | 382/154 |
| 2008/0181479 A1* | 7/2008 | Yang et al. | 382/131 |
| 2008/0199064 A1* | 8/2008 | Gerard et al. | 382/131 |
| 2008/0304730 A1* | 12/2008 | Abe | 382/131 |
| 2008/0317316 A1* | 12/2008 | Ohuchi et al. | 382/131 |
| 2009/0069680 A1* | 3/2009 | Abe | 600/440 |
| 2009/0198133 A1* | 8/2009 | Kawagishi et al. | 600/443 |
| 2009/0238404 A1* | 9/2009 | Orderud et al. | 382/103 |
| 2009/0318803 A1* | 12/2009 | Abe et al. | 600/438 |
| 2010/0056919 A1* | 3/2010 | Abe | 600/443 |
| 2010/0195881 A1* | 8/2010 | Orderud et al. | 382/131 |

FOREIGN PATENT DOCUMENTS

| | | | | |
|---|---|---|---|---|
| JP | 2006-61581 A | 3/2006 | | |
| JP | 2007-44499 | 2/2007 | | |
| JP | 2007-319190 A | 12/2007 | | |
| JP | 2010-502245 A | 1/2010 | | |
| WO | WO2007138751 | * 12/2007 | | A61B 8/08 |
| WO | WO 2008/026022 A1 | 3/2008 | | |

OTHER PUBLICATIONS

Japanese Office Action issued May 28, 2013 in Patent Application No. 2008-222648 with English Translation.

* cited by examiner

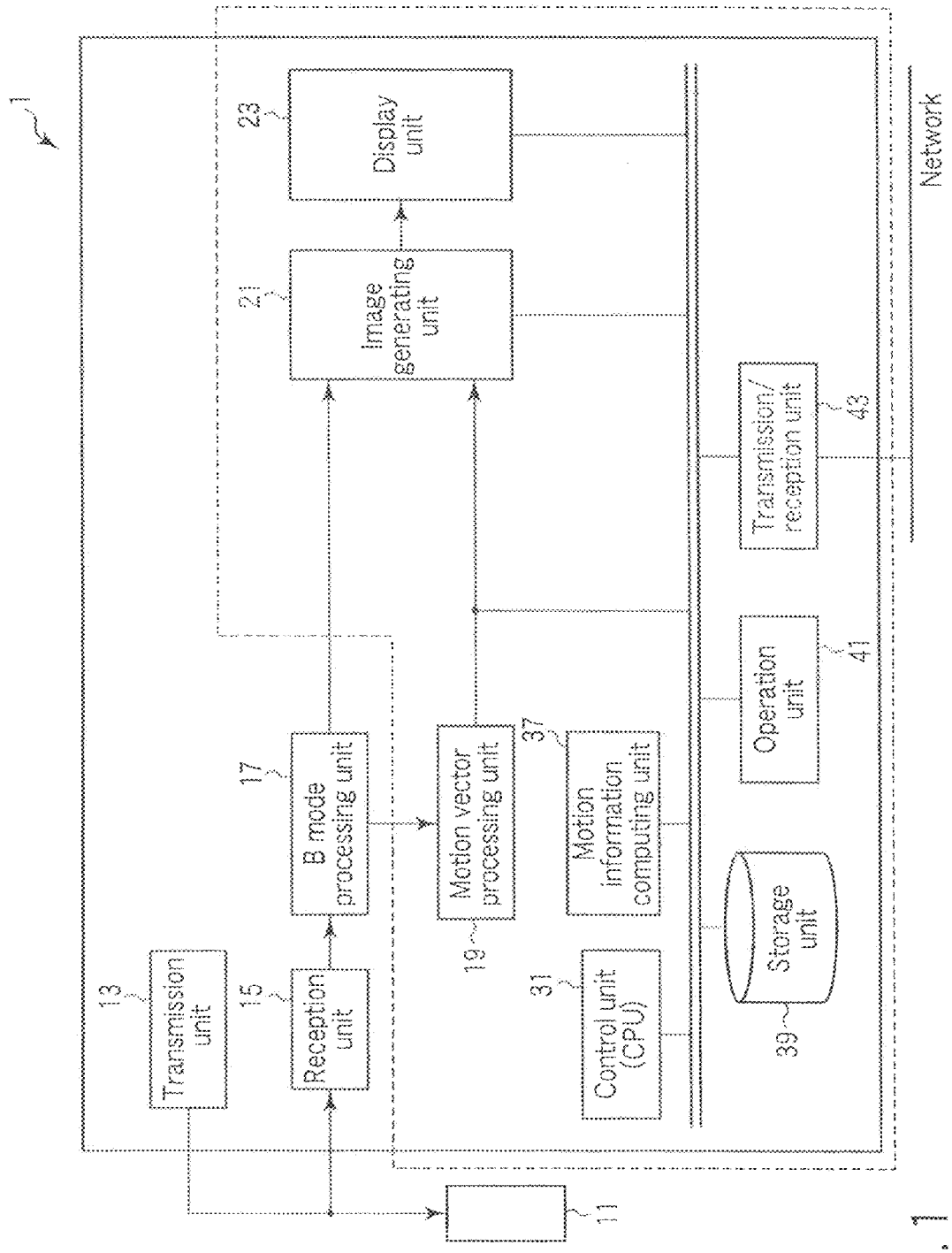
F I G. 1

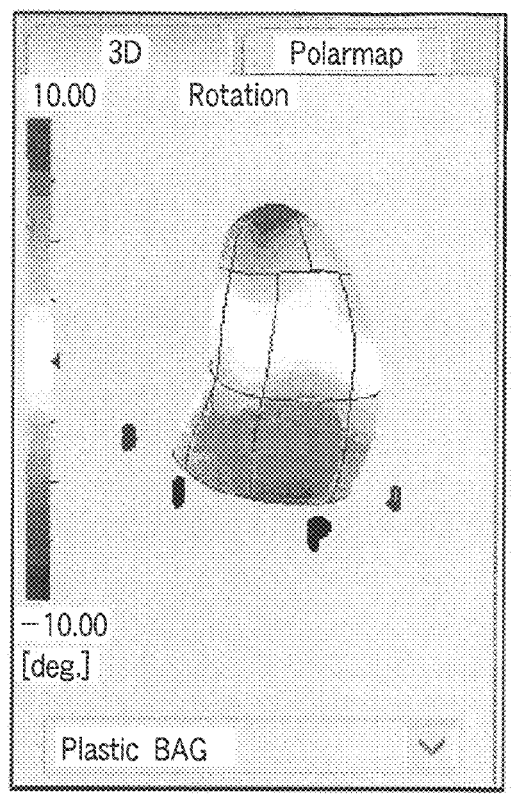
F I G. 7
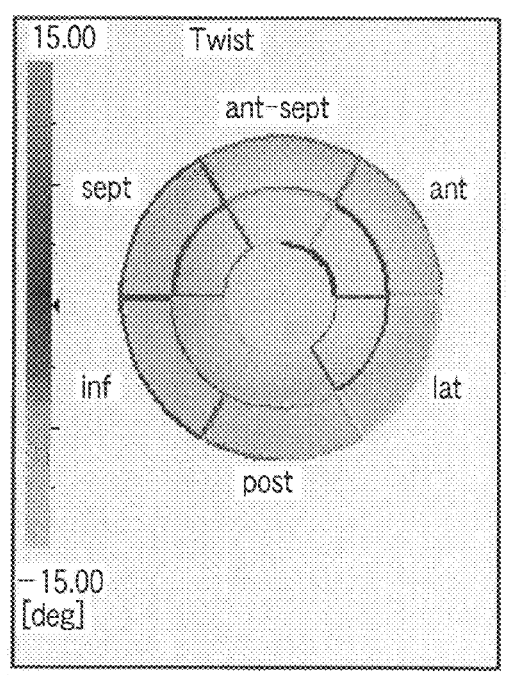
F I G. 8

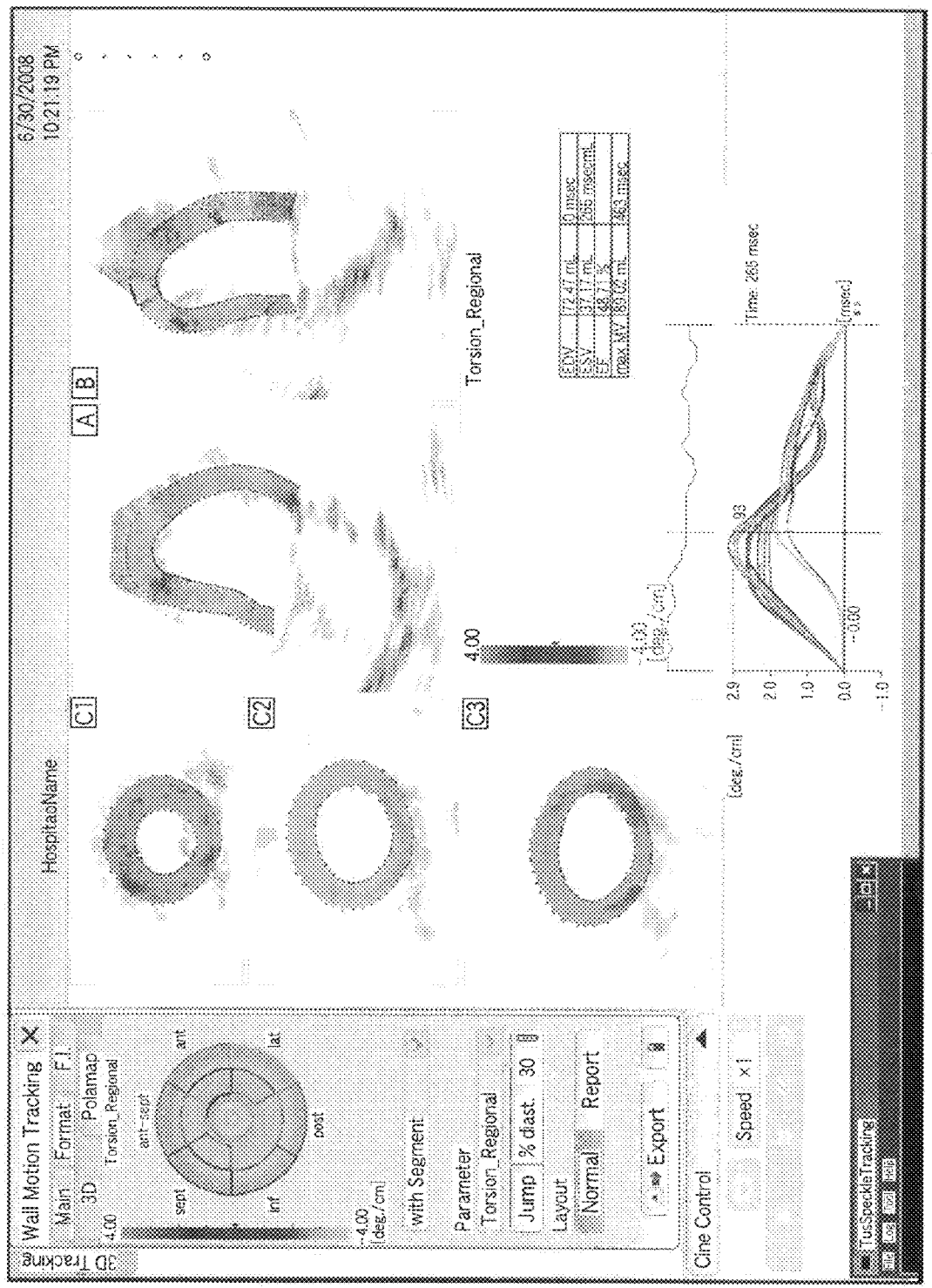
F I G. 11

$$|V_{ij}(t_0) \times V_{ij}(t)| = |V_{ij}(t_0)| \, |V_{ij}(t)| \sin(\theta_{ij}(t))$$

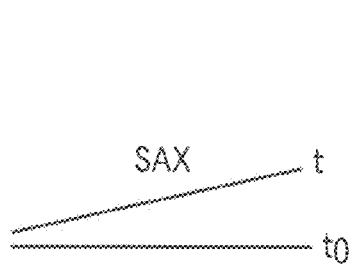
F I G. 16A
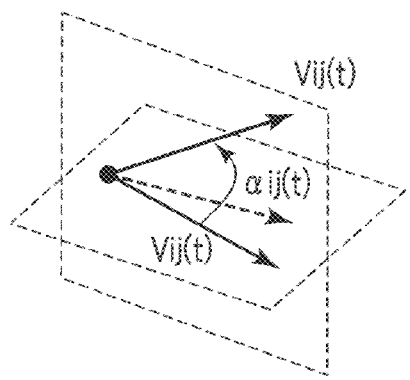
F I G. 16B
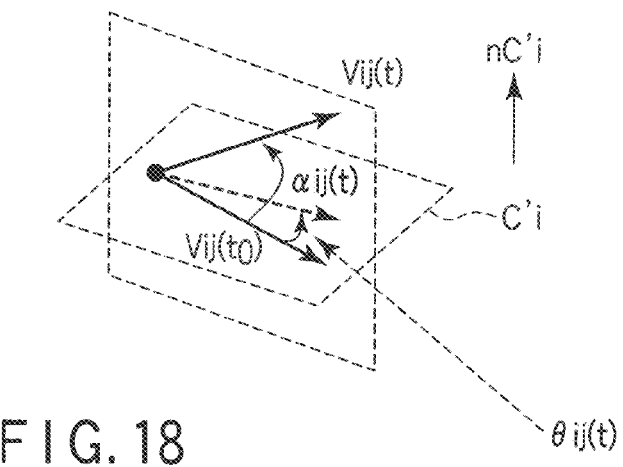
F I G. 18
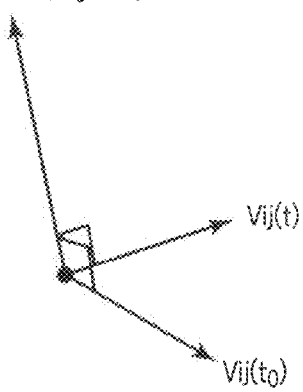
F I G. 19
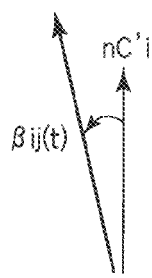
$\langle nC'i, CPij(t)\rangle = |nC'i||CPij(t)|\cos(\beta ij(t))$
F I G. 20

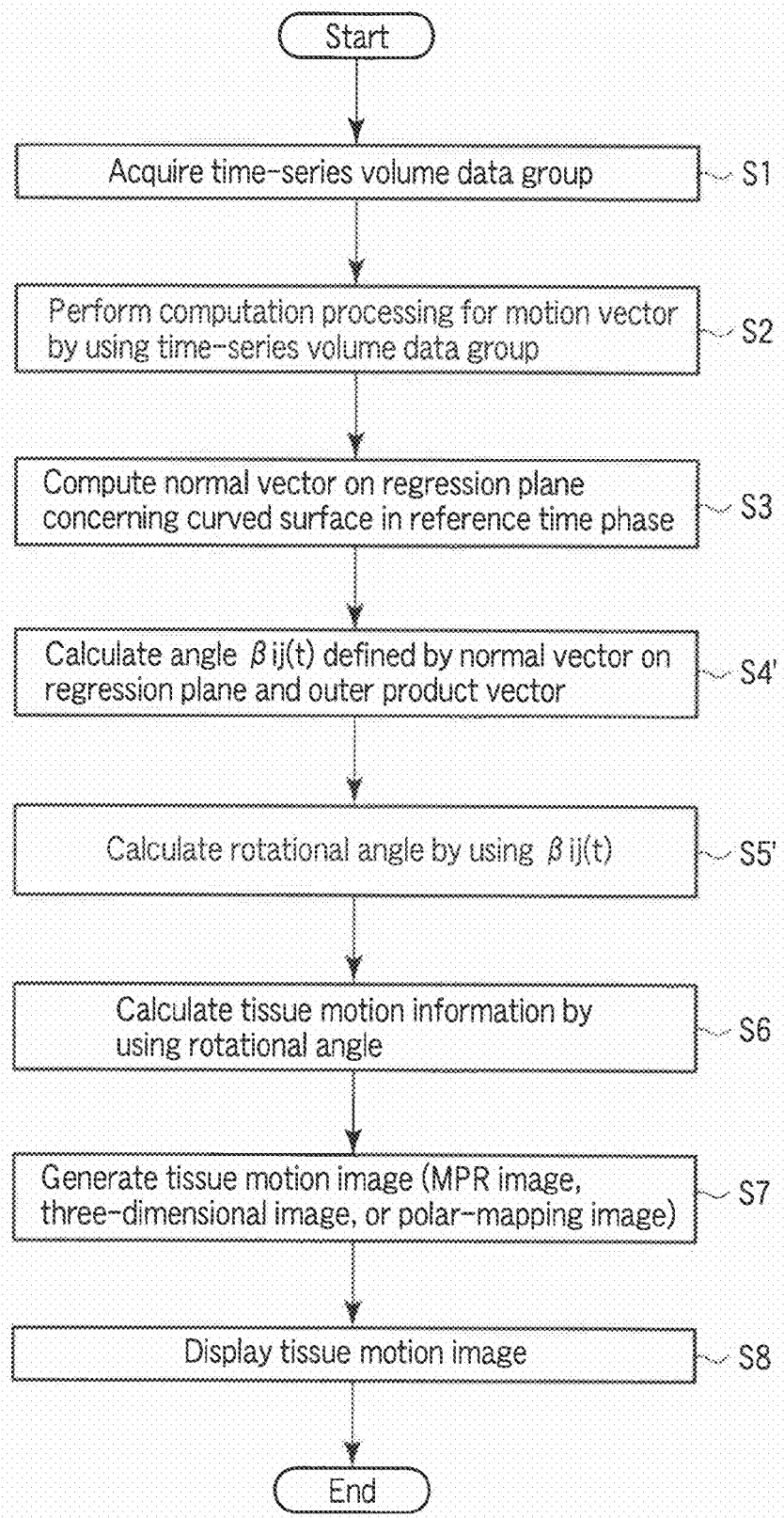
F I G. 17

ULTRASONIC DIAGNOSIS METHOD AND APPARATUS IMAGE PROCESSING FOR CALCULATING ROTATIONAL ANGLES IN A SPACE BY THREE-DIMENSIONAL POSITION TRACKING

CROSS-REFERENCE TO RELATED APPLICATIONS

This application is based upon and claims the benefit of priority from prior Japanese Patent Application No. 2008-222648, filed Aug. 29, 2008, the entire contents of which are incorporated herein by reference.

BACKGROUND OF THE INVENTION

1. Field of the Invention

The present invention relates to an ultrasonic diagnosis apparatus, image processing apparatus, and image processing method for the accurate extraction of rotational components in evaluating motion information concerning the rotation of a tissue using a three-dimensional image.

2. Description of the Related Art

It is very important for the diagnosis of a living tissue such as cardiac muscle to objectively and quantitatively evaluate the function of the tissue. Recently, various quantitative evaluation methods using ultrasonic diagnosis apparatuses and the like have been attempted mainly on the heart as an example. For example, as disclosed in Jpn. Pat. Appln. KOKAI Publication No. 2003-250804, there has recently been commercialized a technique called speckle tracking, which is a technique of calculating local wall motion information such as displacement or strain while performing local pattern matching in images. In addition, Jpn. Pat. Appln. KOKAI Publication No. 2007-44499 discloses a technique of obtaining three-dimensional rotation or twist as wall motion information in a short-axis plane.

There has not currently been established any specific method of obtaining rotational angles in a space accompanied by three-dimensional position tracking in quantitative evaluation of the rotational motion of a tissue. For example, Jpn. Pat. Appln. KOKAI Publication Nos. 2003-250804 and 2007-44499 described above define only a rotational angle in a short-axis plane (two-dimensional plane).

In the calculation of rotational angles in a space accompanied by three-dimensional position tracking, the following problems arise. That is, when three-dimensional position tracking is to be performed, a surface for the definition of a rotational angle is not necessarily limited to a plane but may be a curved surface. In addition, a region whose rotational angle is to be obtained may move in a direction perpendicular to a surface for the definition of a rotational angle. Quantitatively evaluating the rotational motion of a tissue without the consideration of these situations will result in overestimation of a rotational angle when there is unevenness in a shortening motion in the circumferential direction or a spatially uneven motion component in a direction perpendicular to the rotating direction accompanying a shear motion component.

BRIEF SUMMARY OF THE INVENTION

The present invention has been made in consideration of the above situation, and has as its object to provide an ultrasonic diagnosis apparatus, image processing apparatus, and image processing method which can accurately extract rotational components in a three-dimensional space, as compared with the prior art, in evaluating motion information concerning the rotation of a tissue.

According to an aspect of the present invention, there is provided that an ultrasonic diagnosis apparatus comprising:

a data acquisition unit which acquires, as volume data over at least one heartbeat, a reception signal obtained by scanning a heart with ultrasonic waves;

a setting unit which sets a region of interest of cardiac muscle in a predetermined cardiac time phase in the volume data over at least one heartbeat;

a computing unit which computes local three-dimensional motion vector information concerning the region of interest of cardiac muscle;

a tracking unit which acquires three-dimensional position information of the region of interest of cardiac muscle over at least one heartbeat by tracking a three-dimensional position of the region of interest of cardiac muscle in a cardiac time phase other than the predetermined cardiac time phase by using the local three-dimensional motion vector information;

a rotational angle computing unit which computes a rotational angle at a local position on a curved surface in a circumferential direction of the heart, from which an influence caused when at least one of the curved surface in the circumferential direction and a motion component in a long-axis direction of the heart is uneven in the circumferential direction is removed;

a motion information acquisition unit which acquires tissue motion information concerning rotation by using the rotational angle; and a display unit which displays the tissue motion information concerning the rotation in a predetermined form.

According to another aspect of the present invention, there is provided that an image processing apparatus comprising:

a storage unit which stores volume data concerning a heart which is acquired over at least one heartbeat;

a setting unit which sets a region of interest of cardiac muscle in a predetermined cardiac time phase in the volume data over at least one heartbeat;

a computing unit which computes local three-dimensional motion vector information concerning the region of interest of cardiac muscle;

a tracking unit which acquires three-dimensional position information of the region of interest of cardiac muscle over at least one heartbeat by tracking a three-dimensional position of the region of interest of cardiac muscle in a cardiac time phase other than the predetermined cardiac time phase by using the local three-dimensional motion vector information;

a rotational angle computing unit which computes a rotational angle at a local position on a curved surface in a circumferential direction of the heart, from which an influence caused when at least one of the curved surface in the circumferential direction and a motion component in a long-axis direction of the heart is uneven in the circumferential direction is removed;

a motion information acquisition unit which acquires tissue motion information concerning rotation by using the rotational angle; and a display unit which displays the tissue motion information concerning the rotation in a predetermined form.

According to yet another aspect of the present invention, there is provided that an image processing method comprising:

acquiring volume data concerning a heart over at least one heartbeat;

setting a region of interest of cardiac muscle in a predetermined cardiac time phase in the volume data over at least one heartbeat;

computing local three-dimensional motion vector information concerning the region of interest of cardiac muscle;

acquiring three-dimensional position information of the region of interest of cardiac muscle over at least one heartbeat by tracking a three-dimensional position of the region of interest of cardiac muscle in a cardiac time phase other than the predetermined cardiac time phase by using the local three-dimensional motion vector information;

computing a rotational angle at a local position on a curved surface in a circumferential direction of the heart, from which an influence caused when at least one of the curved surface in the circumferential direction and a motion component in a long-axis direction of the heart is uneven in the circumferential direction is removed;

acquiring tissue motion information concerning rotation by using the rotational angle; and displaying the tissue motion information concerning the rotation in a predetermined form.

BRIEF DESCRIPTION OF THE SEVERAL VIEWS OF THE DRAWING

FIG. 1 is a block diagram showing the arrangement of an ultrasonic diagnosis apparatus 1 according to the first embodiment;

FIG. 7 is a view showing another example of the display form of the tissue motion image associated with the rotational angle;

FIG. 8 is a view showing still another example of the display form of the tissue motion image associated with the rotational angle;

FIG. 11 is a view showing another example of the display form of the tissue motion image associated with the torsion rate;

FIGS. 16A and 16B are views for explaining the operation and effects of the ultrasonic diagnosis apparatus according to the embodiment;

FIG. 17 is a flowchart showing a procedure for rotational angle generation processing according to the second embodiment;

FIG. 18 is a view for explaining the concept of rotational angle generation processing according to the second embodiment;

FIG. 19 is a view for explaining the concept of rotational angle generation processing according to the second embodiment; and FIG. 20 is a view for explaining the concept of rotational angle generation processing according to the second embodiment.

DETAILED DESCRIPTION OF THE INVENTION

Figure 2:
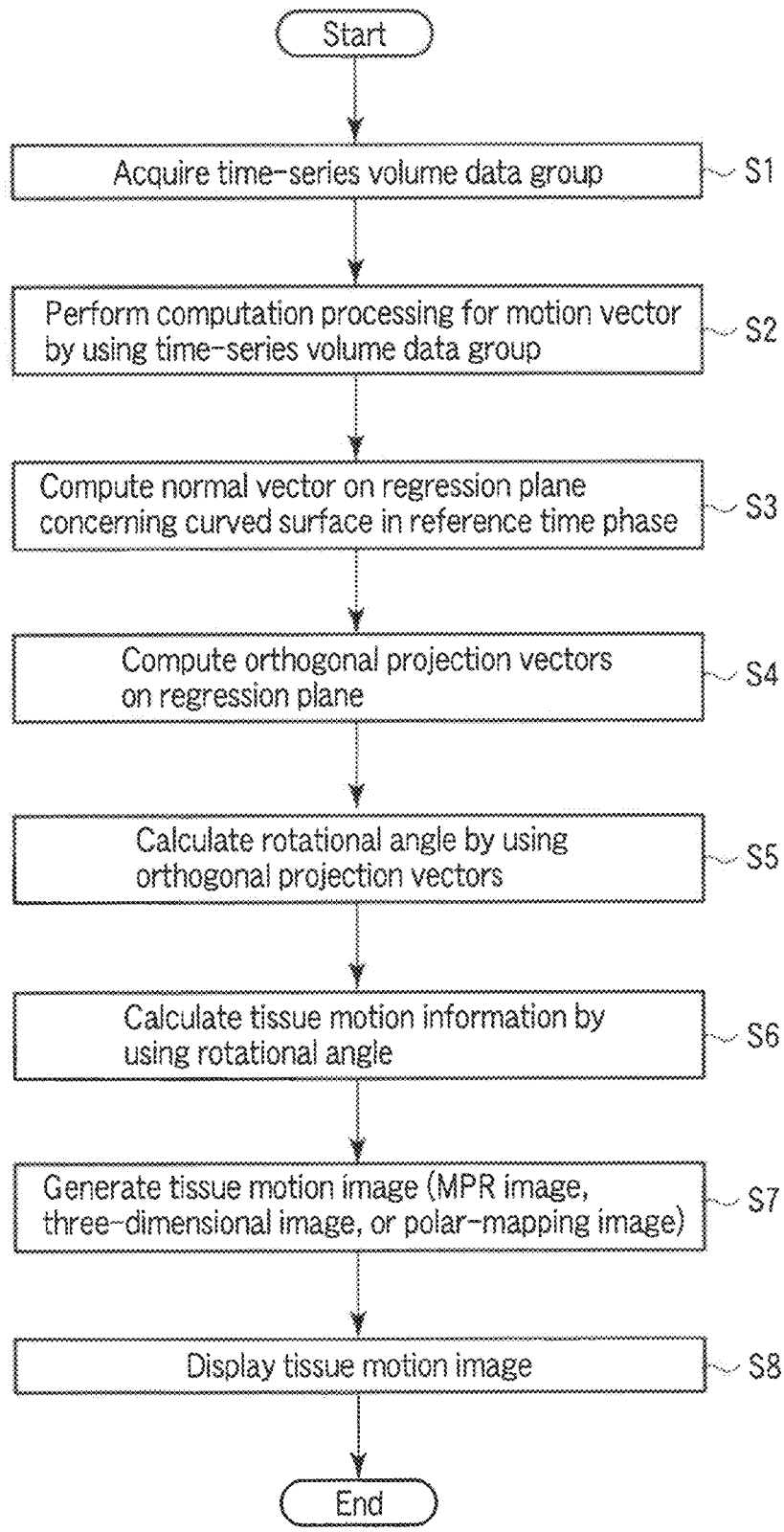
FIG. 2 is a flowchart showing a procedure for motion information generation processing according to the first embodiment.

An embodiment of the present invention will be described with reference to the views of the accompanying drawing. Note that the same reference numerals denote constituent elements having almost the same functions and arrangements, and a repetitive description will be made only when required.

This embodiment exemplifies a case in which the technical idea of the present invention is applied to an ultrasonic diagnosis apparatus. However, the technical idea of the present invention is not limited to this, and can be applied to, for example, an ultrasonic image processing apparatus using a workstation, personal computer, or the like.

The functions implemented by the respective constituent elements according to this embodiment, more particularly, the functions implemented by a motion vector processing unit 19, an image generating unit 21, and a motion information computing unit 37 which will be described later can also be implemented by installing software programs to execute processes similar to those executed by the respective constituent elements in a computer such as a workstation, an ultrasonic diagnostic apparatus having a computer function, or the like, and loading them into a memory. In this case, the programs which can cause the computer to execute the corresponding techniques can be distributed by being stored in recording media such as magnetic disks (floppy® disks, hard disks, and the like), optical disks (CD-ROMs, DVDs, and the like), and semiconductor memories.

FIG. 1 is a block diagram showing the arrangement of an ultrasonic diagnosis apparatus 1. The ultrasonic diagnosis apparatus 1 includes an ultrasonic probe 11, a transmission unit 13, a reception unit 15, a B mode processing unit 17, the motion vector processing unit 19, the image generating unit 21, a display unit 23, a control unit (CPU) 31, the motion information computing unit 37, a storage unit 39, an operation unit 41, and a transmission/reception unit 43. Note that when the present invention is to be applied to an ultrasonic image processing apparatus, the elements enclosed by, for example, the dotted line in FIG. 1 are the constituent elements of the apparatus.

The ultrasonic probe 11 includes a plurality of piezoelectric transducers which generate ultrasonic waves based on driving signals from the ultrasonic transmission unit 13 and convert reflected waves from an object into electrical signals, a matching layer provided for the piezoelectric transducers, and a backing member which prevents ultrasonic waves from propagating backward from the piezoelectric transducers. When ultrasonic waves are transmitted from the ultrasonic probe 11 to the object, various harmonic components are generated due to the nonlinearity and the like of a living tissue upon propagation of the ultrasonic waves. Fundamental waves and harmonic components constituting transmission ultrasonic waves are scattered backward by acoustic impedance boundaries of a tissue in the living body, micro-scattering, and the like, and are received as reflected waves (echoes) by the ultrasonic probe 11.

The transmission unit 13 includes a delay circuit and a pulser circuit (none are shown). The pulser circuit repeatedly generates rate pulses for the formation of transmission ultrasonic waves at a predetermined rate frequency fr Hz (period: 1/fr sec). The delay circuit gives each rate pulse the delay time required to focus an ultrasonic wave into a beam for each channel and determine a transmission directivity. The transmission unit 13 applies a driving pulse to each transducer to form an ultrasonic beam toward a predetermined scanning line at the timing based on this rate pulse.

The reception unit 15 includes an amplifier circuit, A/D converter, and adder (none are shown). The amplifier circuit amplifies echo signals received via the probe 11 on a channel basis. The A/D converter gives each amplified echo signal the delay time required to determine a reception directivity. The adder then performs addition processing. This addition generates an ultrasonic echo signal corresponding to a predetermined scanning line.

The B mode processing unit 17 generates B mode signal corresponding to the amplitude strength of the ultrasonic echo by performing envelope detection processing for the ultrasonic echo signal received from the reception unit 15.

The motion vector processing unit 19 detects the moving position of a tissue by using pattern matching processing between two three-dimensional image data in different time phases or two volume data in different time phases, and obtains the motion vector (or the velocity) of each tissue based on the moving position. More specifically, the motion vector processing unit 19 can obtain the motion vector of the tissue by obtaining, with regard to a region of interest in one three-dimensional image data, a region of interest in the other three-dimensional image data which has the highest similarity and obtaining the distance between the regions of interest. The motion vector processing unit 19 can also obtain the moving velocity of the tissue by dividing the magnitude of this motion vector (i.e., the moving amount) by the time difference (the time difference between the volume data) between the frames of the three-dimensional image data. Performing this processing at each position on three-dimensional image data frame by frame (or at each position on three-dimensional image data volume by volume) can acquire spatiotemporal distribution data (motion vector information) associated with the displacement (motion vector) of the tissue or the velocity of the tissue.

The image generating unit 21 generates a two-dimensional or three-dimensional B mode ultrasonic image by MPR applied to a B mode signal. In addition, the image generating unit 21 uses motion information concerning the rotation which is generated by the motion information computing unit 37 to generate an image (tissue motion information image) having the motion information superimposed at a corresponding position on the ultrasonic image.

The display unit 23 displays an ultrasonic image, tissue motion information image, rotation difference information, and the like in predetermined forms based on video signals from the image generating unit 21, as will be described later. The display unit 23 also displays a marker for indicating an anatomical position on an image and a color bar indicating the magnitude of a color-coded physical quantity.

The control unit (CPU) 31 has a function of an information processing apparatus (computer), and statically or dynamically controls the operation of this ultrasonic diagnostic apparatus. In particular, the control unit 31 executes a motion information generating function (to be described later) by loading a dedicated program stored in the storage unit 39 into a memory (not shown).

The motion information computing unit 37 extracts rotational components of a tissue in a three-dimensional space by using a regression plane or the like in processing (motion information generation processing) complying with the motion information generating function (to be described later). By using the extracted components, the motion information computing unit 37 computes motion information concerning rotation (e.g., motion information (Rotation or Rotation rate) concerning an area barycenter in a short-axis plane, motion information (Twist or Twist rate) as the rotation difference between different short-axis planes, and motion information (Torsion or Torsion rate) obtained by normalizing twist information with the distance between short-axis planes).

The storage unit 39 includes a recording medium such as a magnetic disk (a floppy® disk, hard disk, or the like), an optical disk (a CD-ROM, DVD, or the like), or a semiconductor memory, and a device to read out information recorded on them. The storage unit 39 stores transmission/reception conditions, a predetermined scan sequence, raw data and ultrasonic image data corresponding to each time phase (e.g., tissue image data obtained by imaging in the tissue Doppler mode, the B mode, and the like), volume data generated in advance for each time phase, spatiotemporal distribution data concerning the motion vector or velocity of a tissue, a program for implementing the motion information generating function (to be described later), diagnosis information (a patient ID, findings by a doctor, and the like), a diagnosis protocol, a body mark generating program, and the like.

The operation unit 41 is connected to the apparatus body and includes a mouse, trackball, mode switch, and keyboard which are used to, for example, input various instructions from the operator, an instruction to set a region of interest (ROI), and instructions to set various image quality conditions, and select arbitrary tissue motion information.

The transmission/reception unit 43 is a device to transmit/receive information to/from another apparatus via a network. The transmission/reception unit 43 can transfer data such as ultrasonic images, analysis results, and the like obtained by the ultrasonic diagnosis apparatus 1 to another apparatus via the network.

(Motion Information Generating Function)

The motion information generating function which the ultrasonic diagnosis apparatus 1 has will be described next. This function defines a normal vector on a regression plane in a three-dimensional space with regard to a moving tissue typified by a cardiac wall, accurately extracts rotational components of the tissue by using the normal vector on the regression plane, and generates motion information concerning rotation by using the extracted components.

Note that, for the sake of a concrete description, this embodiment will exemplify the motion information generating function in a case in which a diagnosis target is the heart. However, the target to which this motion information generating function is applied is not limited to the heart, and can be any region as long as it is a tissue that nearly makes rotational motion.

FIG. 2 is a flowchart showing a procedure for processing (motion information generation processing) complying with this motion information generating function. This procedure will be described below with reference to FIG. 2.

[Acquisition of Time-Series Volume Data: Step S1]

First of all, this function acquires time-series volume data (to be referred to as a "time-series volume data group" hereinafter) over at least an interval of one heartbeat in a desired observation region of the heart or the entire heart of a given patient (step S1). That is, the function acquires time-series (corresponding to at least one heartbeat) volume data concerning a desired observation region in the heart of a given patient with reference to a given time from an apical approach using a two-dimensional array probe or the like.

[Generation of Motion Vector Information: Step S2]

Figure 3:
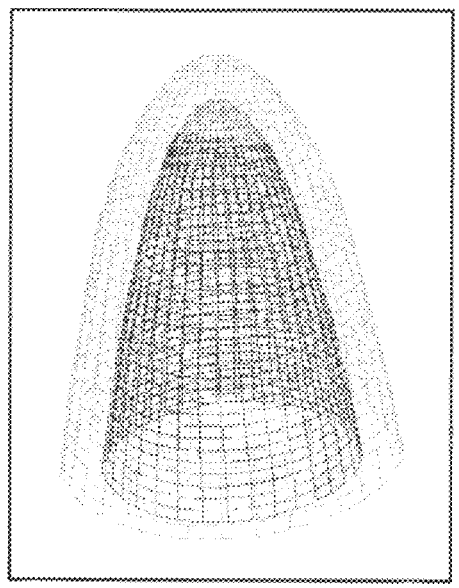
FIG. 3 is a view for explaining a coordinate system for the computation of rotational information.

The function then generates motion vector information (step S2). That is, a motion vector processing unit 32 sets the interface of a myocardial region (preferably, for example, the intima of the heart), in volume data in reference time phase t=t0 (preferably, for example, an end-diastolic period at which P and R waves are generated) of volume data corresponding to each time phase corresponding to one or more heartbeats, which constitute the acquired time-series volume data group, based on an instruction or the like from the user. The motion vector processing unit 32 computes spatiotemporal motion vector information by temporally tracking the position of the vertex of each mesh, obtained by segmenting the set interface into meshes as shown in, for example, FIG. 3, by three-dimensional pattern matching processing.

[Computation of Normal Vector on Regression Plane Concerning Curved Surface in Referent Time Phase: Step S3]

Figure 4:
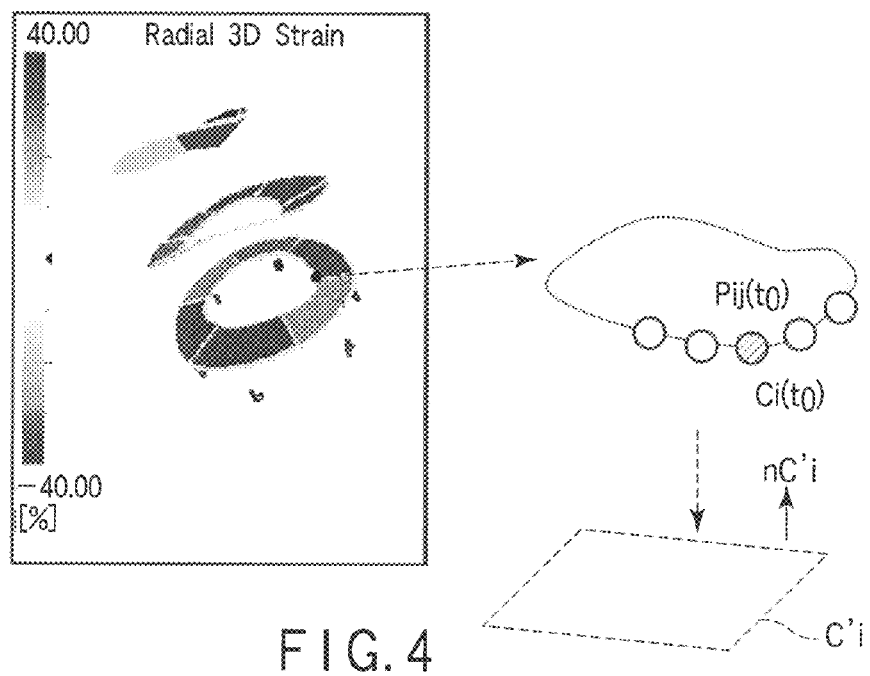
FIG. 4 is a view for explaining the definition of a normal vector on a regression plane concerning a given curved surface in a reference time phase.

The motion information computing unit 37 then computes a normal vector on a regression plane concerning a curved surface in the reference time phase (step S3). That is, as shown in FIG. 4, in accordance with initial setting or an instruction from the operator, the motion information computing unit 37 selects one curved surface Ci(t0) (where i is a suffix indicating a short-axis level) from meshes in the short-axis direction in reference time phase t=t0, and computes a unit normal vector nC'i on a regression plane C'i by using each vertex Pij(t0) (where j is a suffix indicating a position in the circumferential direction) on the curved surface Ci(t0). It is preferable to estimate the unit normal vector nC'i on the regression plane C'i by the least squares method with two variables using the positions of m points Pij(t0) on the short-axis curved surface Ci(t0). In such a calculation technique, a distance ε between a central position Gi(t0) as the average position of m vertexes Pij(t0) determined afterward and the regression plane C'i becomes sufficiently small. This technique is therefore preferably used considering that the central position Gi(t0) becomes a reference position for a vector Vij(t0).

[Computation of Orthogonal Projection Vectors on Regression Plane: Step S4]

The motion information computing unit 37 computes orthogonal projection vectors on the regression plane C'i with regard to each vertex Pij(t) in each time phase (step S4). First of all, the motion information computing unit 37 obtains a central position Gi(t) from the average coordinates of each vertex Pij(t) on a curved surface Ci(t) according to equation (1) given below:

$$Gi(t) = (1/m)\Sigma Pij(t) \tag{1}$$

where $\Sigma$ takes the sum of $1 \le j \le m$, and m is the number of segmentations in the circumferential direction.

Figure 5:
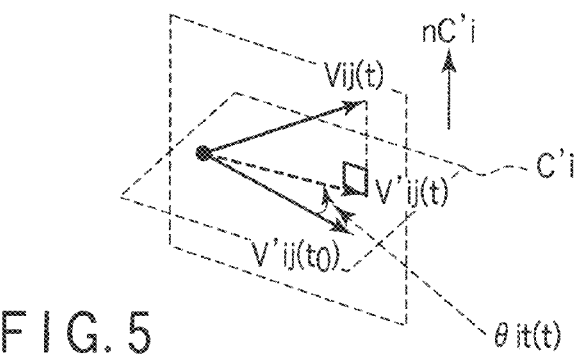
FIG. 5 is a view for explaining orthogonal projection vectors on a regression plane and the definition of a rotational angle using the orthogonal projection vectors.

As shown in FIG. 5, the motion information computing unit 37 then computes an orthogonal projection vector V'ij(t) on the regression plane C'i in each time phase by using equation (2) associated with a position P'ij(t) of the foot of a perpendicular line extending from each vertex Pij(t) to the regression plane C'i.

$$\begin{aligned} V'ij(t) &= P'ij(t) - Gi(t) \\ &= Vij(t) - <nC'i, Vij(t)> *nC'i \end{aligned} \tag{2}$$

where Vij(t)=Pij(t)−Gi(t), and <nC'i, Vij(t)> represents the inner product of nC'i and Vij(t).

[Calculation of Rotational Angle Using Orthogonal Projection Vectors: Step S5]

As shown in FIG. 5, using the projection component vector V'ij(t) at each vertex in each time phase and a projection component vector V'ij(t0) at each vertex in the reference time phase, the motion information computing unit 37 then computes an angle θij(t) defined by the projection component vectors, and acquires a local rotational angle (Rotation) of each vertex in each time phase relative to the reference time phase (step S5).

[Computation of Tissue Motion Information Using Rotational Angles: Step S6]

The motion information computing unit 37 then computes motion information concerning the rotation of the tissue by using the local rotational angles obtained in step S5 (step S6).

For example, a twist angle (Twist) is defined by the rotational angle difference between two curved surfaces in the circumferential direction. In computing a twist angle as tissue motion information, the level of one rotational angle in the long-axis direction is fixed to C0j(t) for i=0 which corresponds to an annulus region, and the level of the other rotational angle in the long-axis direction is set as Cij(t), thereby obtaining a local twist angle Twij(t) according to equation (3). Note that if the unit of rotational angles is [deg.], the unit of twist angles is also [deg.].

$$Twij(t) = \theta ij(t) - \theta 0j(t) \tag{3}$$

In addition, a torsion gradient (Torsion: also called a torsion rate) is defined as the value obtained by dividing the twist angle between two curved surfaces in the circumferential direction by the distance between the two curved surfaces used for the computation of the twist angle. Therefore, the level of one twist angle in the long-axis direction is fixed to C0j(t) for i=0 which corresponds to the annulus region, and the level of the other rotational angle in the long-axis direction is set to Cij(t), thereby obtaining a local torsion gradient TbNij(t) according to equation (4):

$$\begin{aligned} TbNij(t) &= \frac{[Twij(t) - Tw0j(t)]}{Di0j(t)} \\ &= \frac{[\{\theta ij(t) - \theta 0j(t)\} - \{\theta 0j(t) - \theta 0j(t)\}]}{Di0j(t)} \\ &= \frac{[\theta ij(t) - \theta 0j(t)]}{Di0j(t)} \end{aligned} \tag{4}$$

where Di0j(t) represents the distance between Pij(t) and P0j(t). If the unit of Di0j(t) is [cm], the unit of a torsion gradient is [deg./cm]. As is obvious from equation (4), a torsion gradient can be derived from either a twist angle or a rotational angle.

[Generation of Tissue Motion Information Image: Step S7]

This function then generates a time-series mapping image by mapping motion information using the tissue motion information group (step S7). For example, the image generating unit 21 generates a volume rendering image for each time phase by color-coding the generated tissue motion information group and mapping the codes on the corresponding region of the cardiac muscle. Note that a technique of mapping tissue motion information is not limited to volume rendering processing. For example, it is possible to use any kind of image, as long as it has browsability, including a surface rendering image, polar-map image, and MPR image.

[Display of Tissue Motion Image: Step S8]

The display unit 23 then displays the tissue motion image in a predetermined form (step S8).

Figure 6:
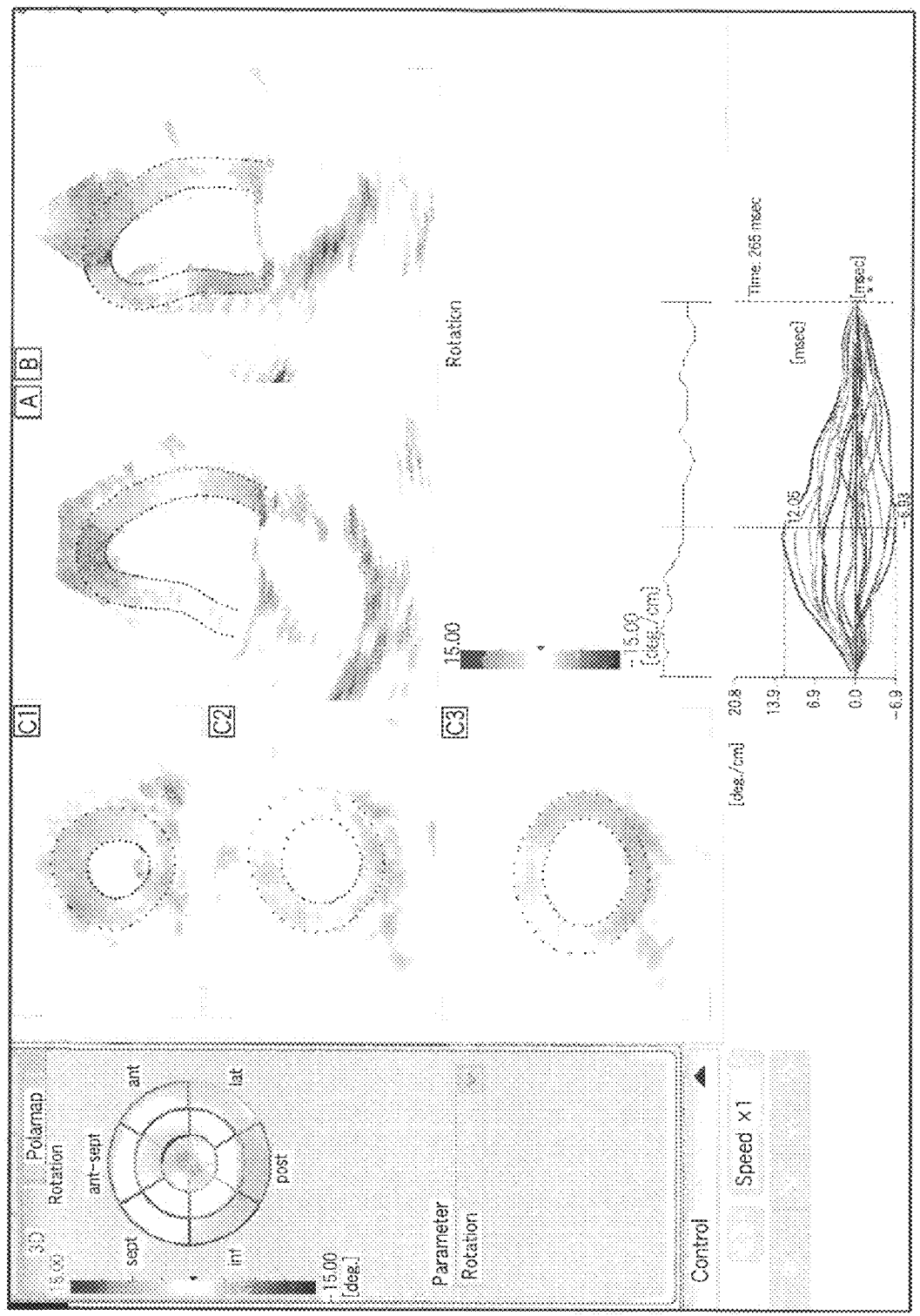
FIG. 6 is a view showing an example of the display form of a tissue motion image associated with the rotational angle calculated by a technique according to the first embodiment.

FIG. 6 is a view showing an example of the display form of a tissue motion image concerning the rotational angle calculated by the technique according to this embodiment. As shown in FIG. 6, reference symbols C1, C2, and C3 denote short-axis MPR images of the left ventricle at different levels; A, an MPR image of the apical four chambers; and B, an MPR image of the cardiac apex (a cross-section near an apical two-chamber image) perpendicular to the image A. In this case, the rotational angles obtained on the intima in a three-dimensional space are converted into the color codes in FIG. 6 (in this example, a bluish color is assigned to counterclockwise rotation which is positive rotation, and a reddish color is assigned to clockwise rotation which is negative rotation), and are displayed upon being superimposed at the position of a region of interest (inside the wavy line indicating the intima-adventitia interface) of the cardiac muscle on the corresponding MPR image. In addition, the rotation information is color-converted and displayed in a polar-map form on the upper left portion of FIG. 6. In order to reduce the influence of local noise, it is preferable to convert these pieces of local rotation information into spatially smooth values by performing smoothing processing in a spatial direction such as a circumferential direction or a long-axis direction.

The time-changing curves on the lower right portion display, as 16 curves, the average values of local rotational angles in the respective areas of 16 segments (area segmentation is indicated within the polar-map display) recommended by ASE. FIG. 6 shows an end-systolic time phase, with a reddish color representing the rotation (clockwise) of the annulus region and a bluish color representing the rotation (counterclockwise) of the apical region. This makes it possible to recognize at a glance that the left ventricle is making a twisting motion in a contraction phase. The polar-map display, in particular, allows to grasp at a glance how the overall left ventricle rotates. Note that a rotational angle is indicated in the unit [deg.].

Although the polar-map form is used as three-dimensional rotation information display, it is possible to perform three-dimensional surface rendering display of the information. In this case, as shown in FIG. 7, it is preferable to color-convert rotational angles and assign and display the resultant data at corresponding positions on the interface reflecting the shape of a region of interest (the intima in this case) of the cardiac muscle as in the above case. Although this display form does not allow to observe at a glance the state of the entire left ventricle as in the case of polar-map display, it is possible to intuitively grasp the shape of the interface of the cardiac muscle and at the same time recognize the state of the rotation of the corresponding region. In this display example, it is preferable to allow observation of a hidden region by rotating a displayed three-dimensional object.

FIG. 8 shows a display example of twist angle information using a polar map. Obviously, the apical region is larger in twist angle than the annulus region, although the absolute values of the respective segments in the circumferential direction differ from each other.

(Modification Concerning Display of Twist)

Figure 9:
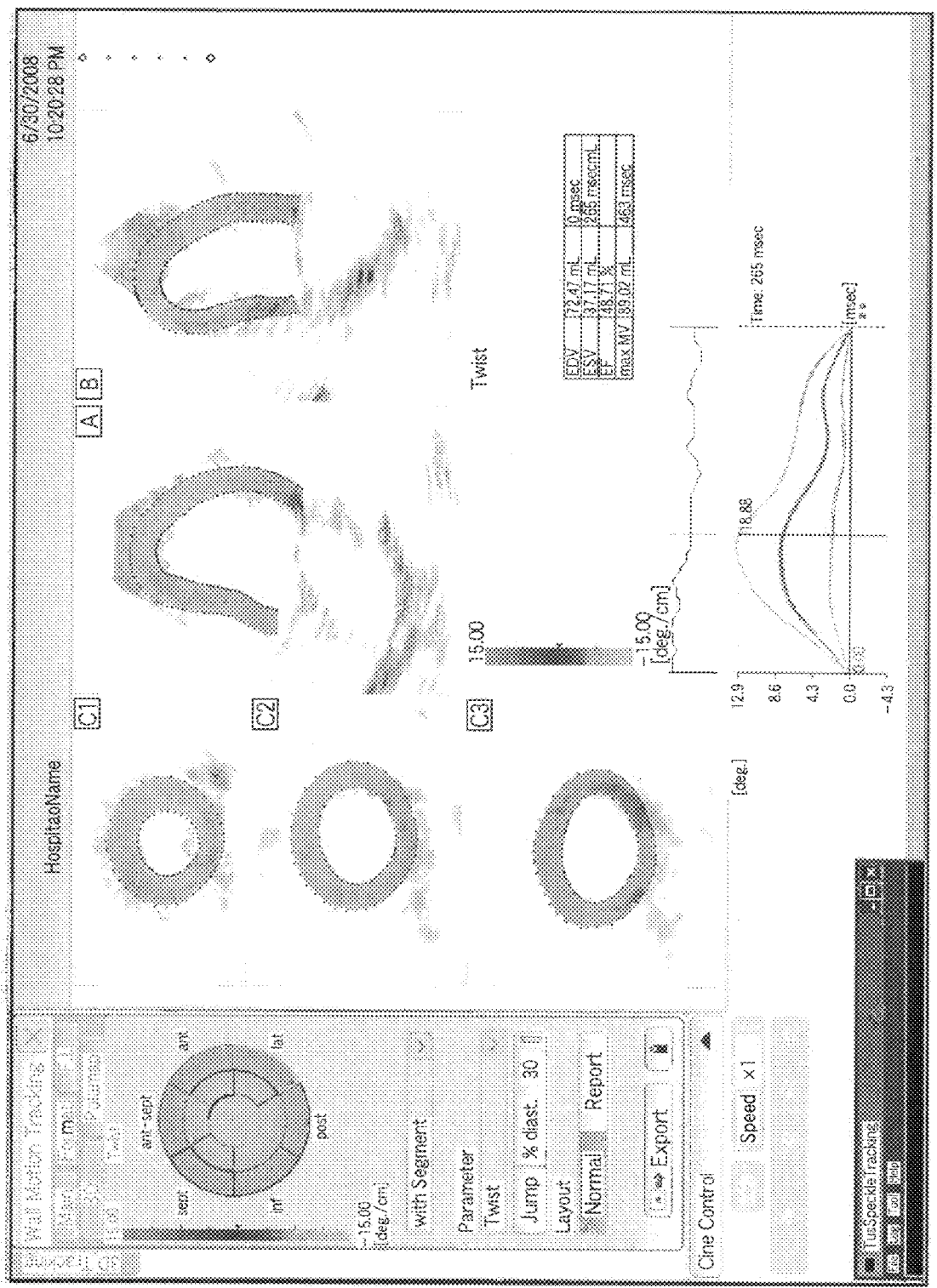
FIG. 9 is a view showing an example of the display form of a tissue motion image associated with the twist angle obtained from the rotational angle calculated by a technique according to the first embodiment.

In general, when clinical twist analysis is performed, which has been studied on a two-dimensional basis, a global (average) twist in the circumferential direction is often evaluated. This is because uneven twist angles are observed at short axes at the same level for the respective segments in the circumferential direction, as recognized in FIG. 8. FIG. 9 shows an example of displaying the result obtained by averaging local twist angles in the circumferential direction as twist angle information based on the above examples. The display form in FIG. 9 is the same as that in FIG. 6 except that the displayed wall motion indexes which are rotational angles are replaced by twist angles. This obviously makes it possible to clearly evaluate the state in which a twist angle gradually increases from the annulus level to the intermediate level and the apical level.

In accordance with the evaluation application, the user may use the latter setting when he/she wants to evaluate overall twist with regard to a segment in the circumferential direction and use the former setting when he/she wants to evaluate local twist with regard to a segment in the circumferential direction.

(Example Concerning Display of Torsion Gradients)

Figure 10:
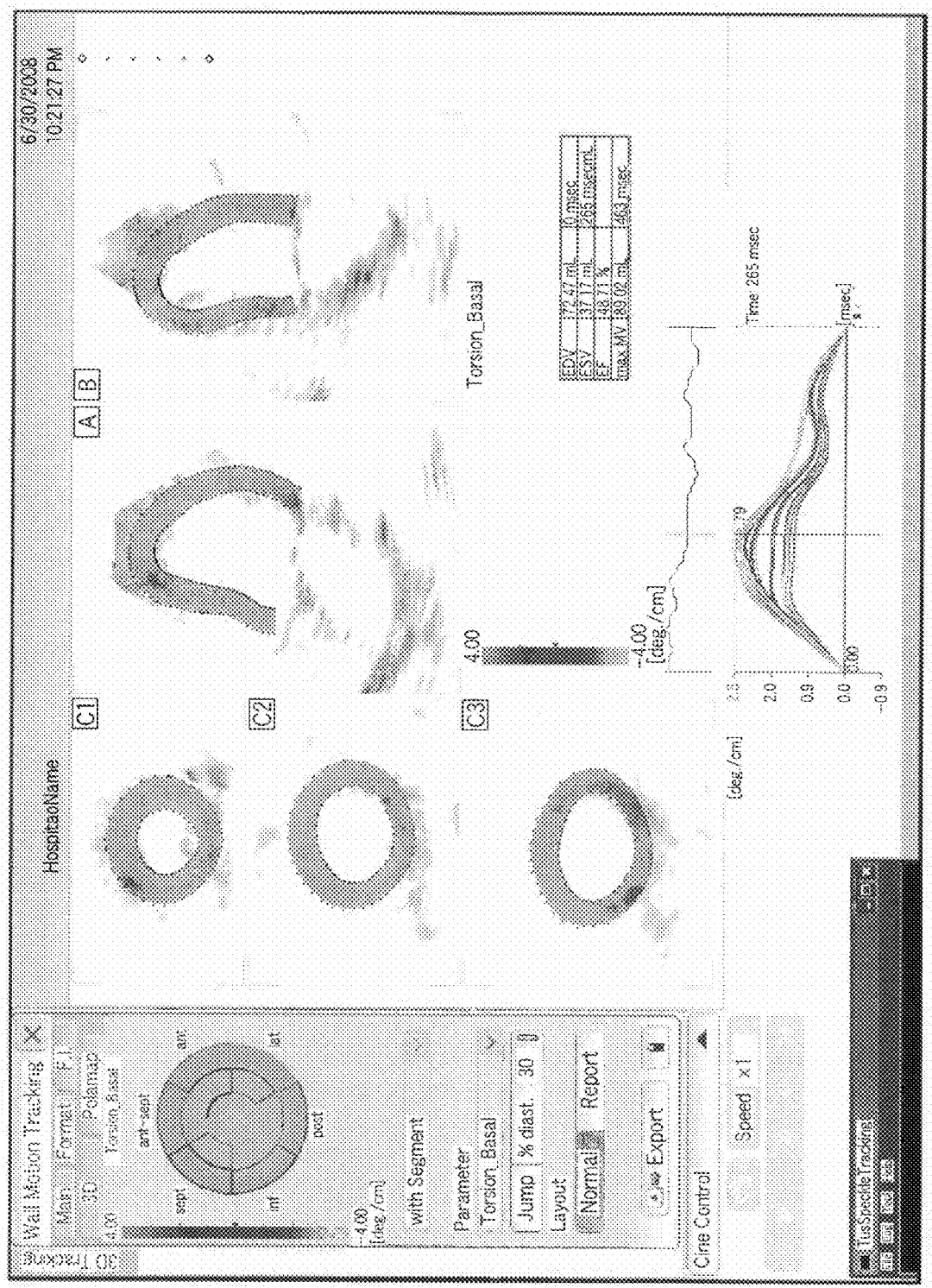
FIG. 10 is a view showing an example of the display form of a tissue motion image associated with the torsion rate obtained from the rotational angle calculated by the technique according to the first embodiment.

FIG. 10 shows a display example of torsion gradient information. FIG. 10 shows an example obtained by using twist angles averaged in the circumferential direction. The apical region is larger in twist angle than the annulus region as in the case of the twist angles in FIG. 9. However, since Di0j(t) varies in value depending on the position in the circumferential direction, the obtained result (see the time-changing curves) exhibits a distribution different from that of twist angles. This indicates the difference in physical meaning between a twist angle and a torsion rate due to the difference in definition. That is, this reflects that even two points (levels) at which the twist angles are the same exhibit different torsion gradients if the distance between the two points changes.

(Modification Concerning Display of Torsion Gradient)

The torsion gradient TbNij(t) in the example concerning the above torsion gradient display is a so-called torsion gradient according to annulus (Basal) basis with the level of one twist angle in the long-axis direction being fixed to C0j(t) with i=0. In this modification, therefore, TrNij(t) is defined by the following equation with the distance between two curved surfaces in the circumferential direction being set to a constant level (the width of 2d+1 from i−d to i+d in the i direction) near the level in the long-axis direction.

$$TrNij(t) = \{TWi+dj(t) - TWi-dj(t)\}/Didj(t)$$

where Didj(t) is the distance between Pi+dj(t) and Pi−dj(t).

The torsion gradient TrNij(t) according to this definition is used, in place of TbNij(t) described above, to evaluate a local Regional torsion gradient in the long-axis direction. If a change in twist angle in the long-axis direction is constant (first-order linear), and the distance between two levels remains the same, TrNij(t) is equal to TbNij(t). In general, however, since a change in twist angle in the long-axis direction is not necessarily first-order linear, the distribution of TrNij(t) differs from that of TbNij(t).

FIG. 11 shows a display example of the local torsion gradient TrNij(t), obtained by the equation given above, by using the display form in FIG. 6. FIG. 11 shows the example obtained by using twist angles averaged in the circumferential direction as indicated by the above modification. As described above, it is obvious that a distribution different from the result of TbNij(t) shown in FIG. 10 is output. Note that the technique of this modification can also be applied to a case in which twist angles are displayed.

(Effects)

According to this ultrasonic diagnosis apparatus described above, with regard to a moving tissue typified by a cardiac wall, a normal vector on a regression plane concerning a reference time phase is defined in a three-dimensional space. This apparatus then calculates orthogonal projection vectors on the regression plane at each vertex Pij(t) in each time phase, and also calculates the angle defined by the orthogonal projection vectors, thereby acquiring a local rotational angle at each vertex Pij(t) in each time phase relative to the reference time phase. Defining a rotational angle by using a regression plane in this manner can accurately extract rotational components of the tissue when a short-axis curved surface does not remain in a plane even in the presence of uneven motion components in a direction perpendicular to the curved surface. The apparatus generates motion information concerning rotation by using the extracted components.

Figure 12:
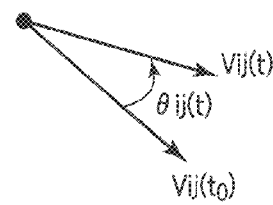
FIG. 12 is a view for explaining an example of a computation definition associated with a rotational angle according to the embodiment.

On the other hand, an angle $\theta ij(t)$ defined by two vectors Vij(t0) and Vij(t) shown in FIG. 12 can be calculated according to equation (5) given below.

$$\theta ij(t) = \sin^{-1}|Vij(t0) \times Vij(t)|/|Vij(t0)|/|Vij(t)| \quad (5)$$

where x represents the outer product of the vectors.

Figure 13:
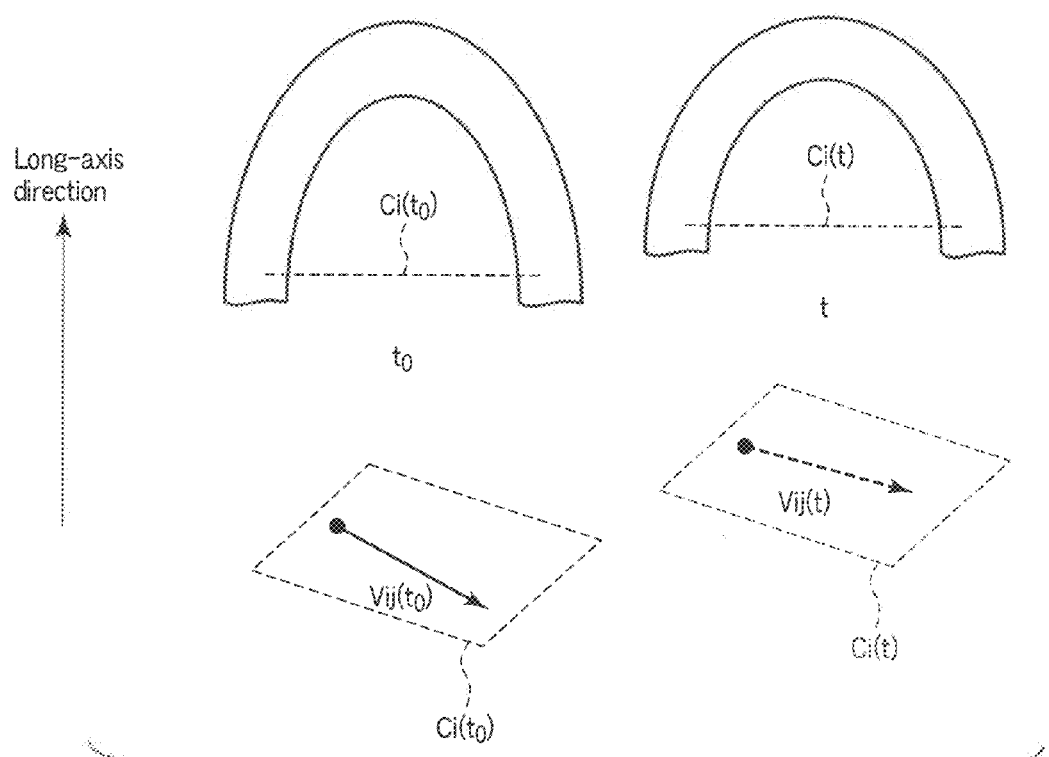
FIG. 13 is a view for explaining the operation and effects of an ultrasonic diagnosis apparatus according to the embodiment.
Figure 14A:
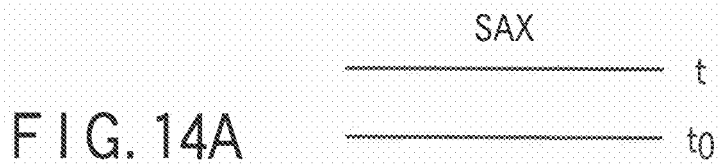
FIGS. 14A and 14B are views for explaining the operation and effects of the ultrasonic diagnosis apparatus according to the embodiment.
Figure 14B:
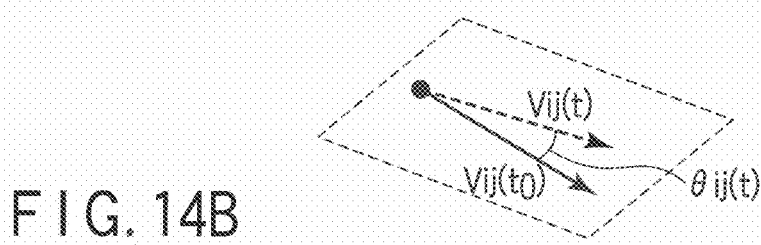
Figure 15:
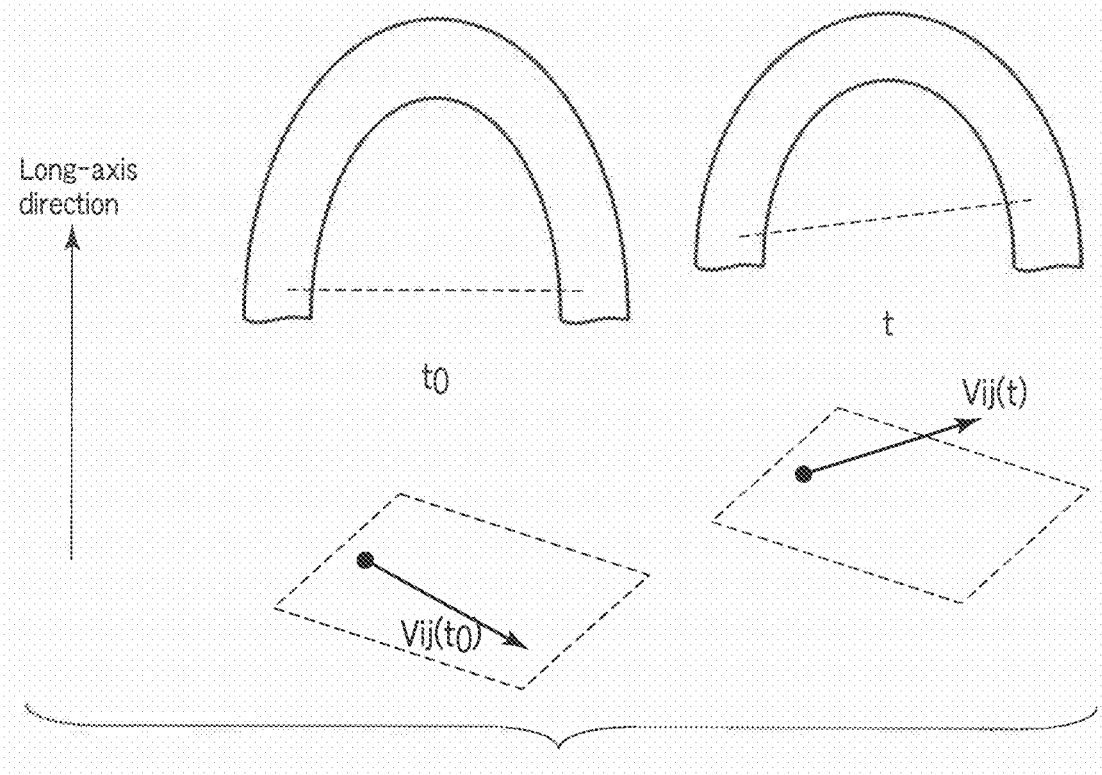
FIG. 15 is a view for explaining the operation and effects of the ultrasonic diagnosis apparatus according to the embodiment.

Assume that the rotational angle of a tissue is calculated according to equation (5). In this case, when the curved surface Ci(t) makes a uniform motion (shortening) toward the central axis with a lapse of time, as shown in FIG. 13, an accurate rotational angle can be obtained, as shown in FIGS. 14A and 14B, even in the presence of a motion perpendicular to a cross-section. If, however, there is unevenness in a shortening motion in the circumferential direction or an uneven motion component in a direction perpendicular to the rotating direction accompanying a shear motion component, as shown in FIG. 15, a rotational angle is overestimated, as shown in FIGS. 16A and 16B. This ultrasonic diagnosis apparatus can accurately calculate rotational components of a tissue even if such an uneven shortening motion or the like occurs in the circumferential direction.

(Second Embodiment)

An ultrasonic diagnosis apparatus according to the second embodiment of the present invention will be described next. This embodiment uses the following technique as a technique of obtaining a probable rotational angle at an arbitrary point on a curved surface when a region in the form of a curved surface at which a rotational angle is to be obtained has an uneven motion in a direction perpendicular to the curved surface. That is, the embodiment obtains "a rotational angle corrected in accordance with the angle defined by the direction of the outer product vector of two vectors defining rotation and a normal vector as a rotation axis on a regression plane C'i concerning a curved surface Ci(t0) in a reference time phase (e.g., t=t0)".

FIG. 17 is a flowchart showing a procedure for motion information generation processing according to the second embodiment. Note that the processing from step S1 to step S3 and the processing from step S6 to step S8 in FIG. 17 are almost the same as those in FIG. 2. The contents of the processing in steps S4' and S5' will be described below.

[Calculation of Angle βij(t) Defined by Normal Vector and Outer Product Vector and Calculation of Rotational Angle θij(t) using βij(t): Steps S4' and S5']

FIGS. 18, 19, and 20 are views for explaining the contents of the processing in steps S4' and S5'. As shown in FIGS. 18 and 19, according to the basic characteristic of a vector product, CPij(t) which is the outer product of a vector Vij(t0) and a vector Vij(t) is also a vector and has a direction perpendicular to both the vector Vij(t0) and the vector Vij(t) (FIG. 18 shows the case of a right-hand system).

Consider an angle βij(t) defined by the vector CPij(t) and a normal vector nC'i (see FIG. 18) on a regression plane C'i. In this case, when βij(t)=0, there is no motion component perpendicular to a curved surface Ci(t) of interest. Obviously, therefore, a rotational angle θij(t) defined by the vector Vij(t0) and the vector Vij(t) is given by θij(t)=βij(t).

In contrast, βij(t)=90° indicates that a point Pij(t) on the curved surface Ci(t) does not move (rotate) in the circumferential direction but moves only in a direction perpendicular to the curved surface. In this case, therefore, θij(t)=0.

As described above, a motion information computing unit 37 calculates the angle βij(t) defined by the vector CPij(t) and the vector nC'i (step S4'). As exemplified by FIG. 20, the motion information computing unit 37 then estimates the rotational angle θij(t) by correcting an angle αij(t) defined by the vector Vij(t0) and the vector Vij(t) by using cos(βij(t)) obtained from the inner product of nC'i and CPij (t) according to equation (6) given below.

$$\theta ij(t) = \alpha ij(t) * \cos(\beta ij(t)) \quad (6)$$

The processing in each of steps S6 to S8 shown in FIG. 2 is executed to display a tissue motion information image in the form shown in FIG. 6 or the like.

This ultrasonic diagnosis apparatus described above acquires an accurate rotational angle, with regard to a moving tissue typified by a cardiac wall, by correcting the angle αij(t) defined by the vector Vij(t0) in a reference time phase t0 and the vector Vij(t) in an arbitrary time phase t by using the angle βij(t) defined by the outer product vector of the vector Vij(t0) and the vector Vij(t) and the normal vector nC'i on the regression plane concerning the reference time phase t0 in a three-dimensional space. When, therefore, a short-axis curved surface does not remain in a plane, this apparatus accurately extracts rotational components of the tissue even in the presence of, for example, uneven motion components in a direction perpendicular to the curved surface, and generates motion information concerning rotation by using the extracted components.

Note that the present invention is not limited to the above embodiments, and constituent elements can be variously modified and embodied at the execution stage within the spirit and scope of the invention. For example, the following are concrete modifications.

(1) For example, each function associated with each embodiment can also be implemented by installing programs to execute the corresponding processing in a computer such as a workstation and loading them in a memory. In this case, the programs which can cause the computer to execute the corresponding techniques can be distributed by being stored in recording media such as magnetic disks (floppy® disks, hard disks, and the like), optical disks (CD-ROMs, DVDs, and the like), and semiconductor memories.

(2) For the sake of easy understanding, each embodiment described above has exemplified the use of ultrasonic image data concerning the heart which is acquired by the ultrasonic diagnosis apparatus. The technical idea of the present invention is not limited to the case in which ultrasonic image data is used. It is possible to compute local rotation information concerning a cardiac tissue in a three-dimensional space by using, for example, magnetic resonance image data concerning the heart which is acquired by using a magnetic resonance imaging apparatus or CT image data concerning the heart which is acquired by using an X-ray computer tomographic apparatus (X-ray CT apparatus).

In addition, various inventions can be formed by proper combinations of a plurality of constituent elements disclosed in the above embodiments. For example, several constituent elements may be omitted from all the constituent elements disclosed in the above embodiments. Furthermore, constituent elements in the different embodiments may be properly combined.

What is claimed is:

1. An ultrasonic diagnosis apparatus comprising:
   a data acquisition processor configured to acquire volume data, corresponding to a plurality of time phases, based on reception signals obtained by scanning a three-dimensional region including at least a part of a heart with ultrasonic waves;
   a setting processor configured to set a short axis plane for the volume data corresponding to at least one of the plurality of time phases;
   a tracking processor configured to set a plurality of three-dimensional positions for the volume data corresponding to a remaining time phase by a three-dimensional tracking of a plurality of positions on the short axis plane;
   a rotational angle computing processor configured to compute a regression plane of the plurality of positions for the remaining time phase, and a rotational angle of a region of interest, on the regression plane for the remaining time phase;
   a motion information acquisition processor configured to acquire tissue motion information concerning rotation by using the rotational angle;
   wherein the motion information acquisition processor is further configured to acquire the tissue motion information concerning a twist angle from a difference between two rotational angles in the circumferential direction by using the rotational angle computed on each of a plurality of curved surfaces in the circumferential direction which are segmented in a long-axis direction of the heart; and
   a display configured to display the tissue motion information concerning the rotation in a predetermined form and the twist angle in a predetermined form.

2. The apparatus according to claim 1, in which the motion information acquisition processor is further configured to acquire the tissue motion information concerning two torsion gradients in the circumferential direction by using the rotational angle computed on each of a plurality of curved surfaces in the circumferential direction which are segmented in a long-axis direction of the heart and three-dimensional position information of the region of interest of cardiac muscle, and which further comprises
   a display configured to display the tissue motion information concerning the torsion gradients in a predetermined form.

3. The apparatus according to claim 1, wherein the motion information acquisition processor is further configured to set a position of one of the two rotational angles in the circumferential direction in a long-axis direction to an annulus region of the heart.

4. The apparatus according to claim 2, wherein the motion information acquisition processor is further configured to set a position of one of the two rotational angles in the circumferential direction in a long-axis direction to an annulus region of the heart.

5. The apparatus according to claim 1, wherein the motion information acquisition processor is further configured to set positions in the long-axis direction for a pair of the two rotational angles in the circumferential direction.

6. The apparatus according to claim 2, wherein the motion information acquisition processor is further configured to set positions in the long-axis direction for a pair of the two rotational angles in the circumferential direction.

7. The apparatus according to claim 1, wherein the rotational angle computing processor is further configured to obtain a central position of rotation of a curved surface in a circumferential direction of the heart in each cardiac time phase,
   calculate a normal vector on the regression plane concerning the curved surface in the circumferential direction in a predetermined cardiac time phase as a reference,
   calculate a vector of a line connecting one arbitrary point on the curved surface for acquisition of the rotational angle in each cardiac time phase and the central position of the rotation,
   calculate an orthogonal projection component vector of the vector of the line on the regression plane by using the normal vector, and
   calculate an angle defined by the orthogonal projection component vector in the time phase as the reference and the orthogonal projection component vector in each cardiac time phase.

8. The apparatus according to claim 1, wherein the rotational angle computing processor is further configured to obtain a central position of rotation of a curved surface in a circumferential direction of the heart in each cardiac time phase,
   calculate a normal vector on the regression plane concerning the curved surface in the circumferential direction in a predetermined cardiac time phase as a reference,
   calculate a vector of a line connecting one arbitrary point on the curved surface for acquisition of the rotational angle in each cardiac time phase and the central position of the rotation,
   calculate an outer product vector of the vector of the line in the predetermined cardiac time phase as the reference and the vector of the line in each time phase, and
   compute a rotational angle at a local position on a curved surface in the circumferential direction in accordance with an angle defined by the normal vector and the outer product vector.

9. The apparatus according to claim 7, wherein the normal vector on the regression plane is estimated by a least squares method using positions of a plurality of points on the curved surface in the circumferential direction.

10. The apparatus according to claim 8, wherein the normal vector on the regression plane is estimated by a least squares method using positions of a plurality of points on the curved surface in the circumferential direction.

11. The apparatus according to claim 1, wherein the motion information acquisition processor is further configured to compute an average value of tissue motion information concerning the rotation in the circumferential direction based on rotational angles computed at a plurality of points on a curved surface in the circumferential direction.

12. An image processing apparatus comprising:
    a memory configured to store volume data, corresponding to a plurality of time phases, based on a three-dimensional region including at least a part of a heart, which is acquired over at least one heartbeat;

a setting processor configured to set a short axis plane for the volume data corresponding to at least one of the plurality of time phases;

a tracking processor configured to set a plurality of three-dimensional positions for the volume data corresponding to a remaining time phase by a three-dimensional tracking of a plurality of positions on the short axis plane;

a rotational angle computing processor configured to compute a regression plane of the plurality of positions for the remaining time phase, and a rotational angle of a region of interest, on the regression plane for the remaining time phase;

a motion information acquisition processor configured to acquire tissue motion information concerning rotation by using the rotational angle;

wherein the motion information acquisition processor configured to acquire the tissue motion information concerning a twist angle from a difference between two rotational angles in the circumferential direction by using the rotational angle computed on each of a plurality of curved surfaces in the circumferential direction which are segmented in a long-axis direction of the heart; and a display configured to display the tissue motion information concerning the rotation in a predetermined form and the twist angle in a predetermined form.

13. The apparatus according to claim 12, wherein the volume data concerning the heart is acquired by one of an ultrasonic diagnosis apparatus, an X-ray computer tomographic apparatus, and a magnetic resonance imaging apparatus.

14. The apparatus according to claim 12, in which the motion information acquisition processor is further configured to acquire the tissue motion information concerning two torsion gradients in the circumferential direction by using the rotational angle computed on each of a plurality of curved surfaces in the circumferential direction which are segmented in a long-axis direction of the heart and three-dimensional position information of the region of interest of cardiac muscle, and which further comprises a display configured to display the tissue motion information concerning the torsion gradients in a predetermined form.

15. The apparatus according to claim 12, wherein the motion information acquisition processor is further configured to set a position of one of the two rotational angles in the circumferential direction in a long-axis direction to an annulus region of the heart.

16. The apparatus according to claim 14, wherein the motion information acquisition processor is further configured to set a position of one of the two rotational angles in the circumferential direction in a long-axis direction to an annulus region of the heart.

17. The apparatus according to claim 12, wherein the motion information acquisition processor is further configured to set positions in the long-axis direction for a pair of the two rotational angles in the circumferential direction.

18. The apparatus according to claim 14, wherein the motion information acquisition processor is further configured to set positions in the long-axis direction for a pair of the two rotational angles in the circumferential direction.

19. The apparatus according to claim 12, wherein the rotational angle computing processor is further configured to obtain a central position of rotation of a curved surface in a circumferential direction of the heart in each cardiac time phase, calculate a normal vector on the regression plane concerning the curved surface in the circumferential direction in a predetermined cardiac time phase as a reference, calculate a vector of a line connecting one arbitrary point on the curved surface for acquisition of the rotational angle in each cardiac time phase and the central position of the rotation, calculate an orthogonal projection component vector of the vector of the line on the regression plane by using the normal vector, and calculate an angle defined by the orthogonal projection component vector in the time phase as the reference and the orthogonal projection component vectors in each cardiac time phase.

20. The apparatus according to claim 12, wherein the rotational angle computing processor is further configured to obtain a central position of rotation of a curved surface in a circumferential direction of the heart in each cardiac time phase, calculate a normal vector on the regression plane concerning the curved surface in the circumferential direction in a predetermined cardiac time phase as a reference, calculate a vector of a line connecting one arbitrary point on the curved surface for acquisition of the rotational angle in each cardiac time phase and the central position of the rotation, calculate an outer product vector of the vector of the line in the predetermined cardiac time phase as the reference and the vector of the line in each time phase, and compute a rotational angle at a local position on a curved surface in the circumferential direction in accordance with an angle defined by the normal vector and the outer product vector.

21. The apparatus according to claim 19, wherein the normal vector on the regression plane is estimated by a least squares method using positions of a plurality of points on the curved surface in the circumferential direction.

22. The apparatus according to claim 20, wherein the normal vector on the regression plane is estimated by a least squares method using positions of a plurality of points on the curved surface in the circumferential direction.

23. The apparatus according to claim 12, wherein the motion information acquisition processor computes an average value of tissue motion information concerning the rotation in the circumferential direction based on rotational angles computed at a plurality of points on a curved surface in the circumferential direction.

24. An ultrasonic diagnostic apparatus control method comprising:

executing, by a computer:

acquiring volume data, corresponding to a plurality of time phases, based on a three-dimensional region including at least a part of a heart over at least one heartbeat;

setting a short axis plane for the volume data corresponding to at least one of the plurality of time phases, setting a plurality of three-dimensional positions for the volume data corresponding to a remaining time phase by a three-dimensional tracking of a plurality of positions on the short axis plane;

computing a regression plane of the plurality of positions for the remaining time phase, and a rotational angle of a region of interest, on the regression plane for the remaining time phase; and acquiring tissue motion information concerning rotation by using the rotational angle;
wherein further acquiring the motion information of a twist angle from a difference between two rotational angles in the circumferential direction by using the rotational angle computed on each of a plurality of curved surfaces in the circumferential direction which are segmented in a long-axis direction of the heart; and
displaying, on a display, the tissue motion information concerning the rotation in a predetermined form and the twist angle in a predetermined form.

* * * * *